US005618887A

United States Patent [19]
Bamford et al.

[11] Patent Number: 5,618,887
[45] Date of Patent: Apr. 8, 1997

[54] FUNCTIONALISATION OF POLYMERS

[75] Inventors: Clement H. Bamford, Prenton; Kadem G. Al-Lamee, Childwall, both of Great Britain

[73] Assignee: The University of Liverpool, Liverpool, Great Britain

[21] Appl. No.: 338,536

[22] PCT Filed: Jun. 4, 1993

[86] PCT No.: PCT/GB93/01195

§ 371 Date: Feb. 3, 1995

§ 102(e) Date: Feb. 3, 1995

[87] PCT Pub. No.: WO93/25587

PCT Pub. Date: Dec. 23, 1993

[30]   Foreign Application Priority Data

Jun. 5, 1992 [GB]   United Kingdom ................... 9211966

[51] Int. Cl.$^6$ ..................................................... C08F 8/08
[52] U.S. Cl. ..................... 525/279; 525/296; 525/333.8; 525/353; 525/366; 525/387; 525/398; 525/401; 525/420; 525/426; 525/437; 525/445; 525/452; 525/455; 525/472
[58] Field of Search ................................... 525/387, 279, 525/296, 353, 366, 398, 401, 420, 426, 437, 445, 452, 455, 472

[56]   References Cited

FOREIGN PATENT DOCUMENTS 1004655   1/1989   Japan .

OTHER PUBLICATIONS

Jabloner et al., "Heterogeneous Grafting of Polypropylene and Physical Properties of Graft Blends", Journ. Poly. Sci., vol. 10, (1972), pp. 763–778.

Kolthoff et al., "The Chemistry of Persulfate. I. The Kinetics and Mechanism of the Decomposition of the Persulfate Ion in Aqueous Medium[1]", Polymer Sci., vol. 73, No. 1, (1946), pp. 3055–3059.

Mino et al., "A New Method for the Preparation of Graft Copolymers. Polymerization Initiated by Ceric Ion Redox Systems", Journ. of Poly. Sci., vol. XXXI, Issue No. 122, (1958), pp. 242–243.

William A. Szabo, "Chlorosulfonyl Isocyanate, Silver Anniversary of a Lively Heterocumulene", Aldrichimica Acta, vol. 10, No. 2, pp. 23–29.

*Primary Examiner*—Bernard Lipman
*Attorney, Agent, or Firm*—Foley & Lardner

[57]   ABSTRACT

A process for the functionalisation of polymers is disclosed. Functionalisation takes place by reacting a polymer with a peroxidant, preferably, the peroxydisulphate or monosulphate or sodium or potassium in an aqueous medium. The hydroxylated polymer can then be reacted with other materials, including biomolecules. Using the method of the inventon, products eg. Catheters or oxygenators can be produced with improved properties hitherto unobtainable.

19 Claims, No Drawings

FUNCTIONALISATION OF POLYMERS

The present invention relates to the functionalisation of polymers. More particularly it relates to the treatment of polymers which do not possess groups normally considered readily reactive. It also relates to the coupling of so-treated polymers which other materials, for example, monomers, polymers, bioactive materials and dyes.

Conventional procedures for activating the surface of, for example, polypropylene include the action of high energy radiation, glow and corona discharges, photoinitiation with the use of a sensitiser such as benzophenone, reaction with ozone, and surface flaming. Some of these procedures have the disadvantage of severely degrading the polymer and the use of non-aqueous media may be necessary.

Early work with polypropylene was aimed at introducing hydroperoxides; thus in DE-A- 1595 808 and GB-A- 1086108 and by Jabloner and Mommar (J. Polymer Sci. A-1, 1972, 10, (763–778)) it was claimed that a cation surfactant and potassium peroxysulphate could be used to achieve wetting and initiate oxidation of polypropylene powder as slurry. The reaction was carried out in the presence of oxygen (e.g. at 30 p.s.i.), at 100° C. Critical importance was attached to the presence of the cationic surfactant and it was stated that an anionic surfactant did not lead to significant hydroperoxidation. Graft copolymerization was subsequently carried out by addition of a redox system (e.g. ferric salt and benzion) and a vinyl monomer at 65° C.

In many other examples the polymer (polypropylene), initiator (e.g. peroxysulphate) and monomer were reacted together. This procedure led to a high yield of homopolymer. Any graft copolymer was probably formed by chain transfer involving initial or propagating radicals and the polymer.

It has now been found possible to functionalise many polymers by an inexpensive and simple method. It has been found possible to provide such a method which takes a relatively short time and can be effected in aqueous media.

According to the present invention there is provided a method of functionalisating of a polymer, which method comprises reacting the polymer in an aqueous medium with an oxidising agent to produce oxygen-centered radicals which are responsible for introducing hydroxyl groups into the polymer, the reaction being carried out in the absence of (a) any additive which is preferentially oxidised or is reactive towards the radicals produced by the oxidising agent, (b) added oxygen and (c) a cationic surfactant.

According to a further aspect of the present invention there is provided a method for the functionalisation of a polymer, which method consists essentially of reacting the polymer with a suitable oxidising agent in an aquous medium.

A suitable oxidising agent is an oxidising agent capable of producing oxygen-centered radicals (i.e. the free radical is on the oxygen atom) in aqueous media. Under appropriate conditions such radicals can be responsible for introducing hydroxyl groups into the polymer, thus producing a functionalisation process. It is important to note that during the oxidation process no additives with readily extractable hydrogen atoms are present.

The oxidising agent usually used in the method of the present invention is a peroxy salt of a metal, preferably a peroxy-disulphate or monosulphate. We have examined the effectiveness of several peroxidants for the hydroxylation of polystyrene and found the following order:

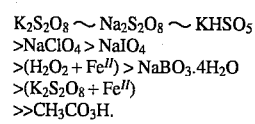

The last compound in the series, that is peracetic acid, has been found to be only very weakly active under the test conditions used.

The present invention will be further described for the sake of convenience with reference to (but in no manner limited to) the use of peroxysulphates as the oxidising agents.

The decomposition of the peroxy moiety may be considered to be in accordance with the equation:

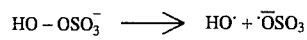

The peroxysulphate may be an alkali metal peroxysulphate, preferably potassium peroxysulphate. A particularly useful potassium compound is a triple salt having the composition $2KHSO_5 \cdot KHSO_4 \cdot K_2SO_4$ such as that sold under the Trade Name "Oxone". The peroxysulphate is employed as an aqueous solution, particularly in connection with biomaterials. The solution may contain other materials provided they do not affect the solubility of the peroxysulphate and are not themselves easily oxidized or reactive towards radicals.

The concentration Of the peroxysulphate in the solution is usually of the order of 2 to 50% weight/volume, preferably 2 to 20% weight/volume, and more preferably 5 to 10% weight/volume.

The reaction is usually carried out at a temperature of from 40° C. to 100° C., more preferably 50° C. to 100° C. The reaction time required depends upon the nature of the polymer and its physical state of division (as more particularly described hereinbelow). The reaction time and the concentration of the oxidising agent are inversely related and the reaction time and temperature are inter-connected.

Potassium peroxydisulphate has long been used as an initiator of free-radical polymerisation in aqueous solution. The reactions involved have been studied by Kolthoff and Miller (I. M. Kolthoff and I. K. Miller, *J.Am. Chem. Soc.*, 1951, 73 3055) who proposed the following mechanism:

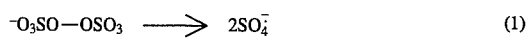

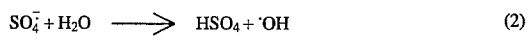

This proposal was supported by experiments with $^{18}O$-labelled water which showed that the oxygen evolved originates from the water.

Various polymers may be functionalised by the method of the present invention. Suitable classes of polymers include:

(a) Olefin polymers such as, for example, polypropylene;

(b) Aliphatic polyesters such as, for example, polyesters containing (esterified) 1,4-cyclohexane dimethanol units (e.g. the polyester sold under the Trade Name "Ecdel");

(c) Polymers containing aromatic rings, such as, for example, poly(ethylene terephthalate);

(d) Polycarbonates;

(e) Vinyl polymers (polymers or copolymers of mono-substituted ethylenes) such as, for example, polystyrene, polyacrylonitrile, poly(vinylchloride) and high density polyethylene;

(f) Polyurethanes such as, for example, aromatic poly(ether urethanes) sold under the Trade Names "Biomer" and "Pellethane" and the aliphatic poly(ether urethane) sold under the Trade Name "Tecoflex";

(g) Nylons, such as, for example nylon 6, nylon 6,6, poly (11-undeccanoamide);

(h) Poly(glycols) or polymers or copolymers containing poly/(glycol) chain segments. The latter include poly (ether urethanes) which are also included in (f) above, the ether constituent being a poly (glycol); and (i) Polyaldehydes.

Whilst again not wishing to be bound by any theory of reaction, the following reaction mechanism may well indicate how the functionalised polymers of the present invention are formed and react with other materials.

Using as an illustration example the polymer polypropylene the functionalisation process involves the abstraction of relatively reactive hydrogen atoms from the polymer as shown below—reactions (4),(5) and (6).

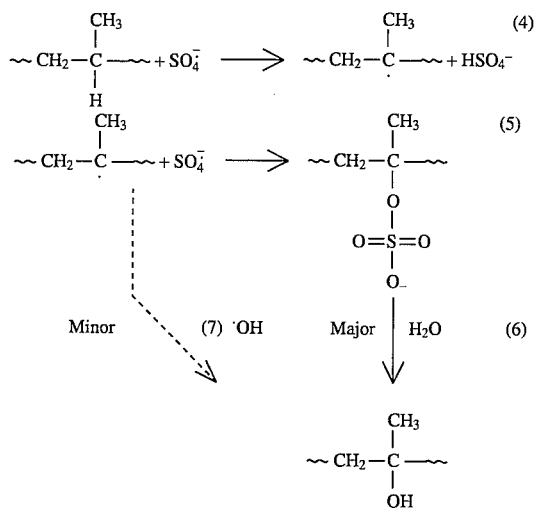

The state of subdivision of the polymer to be functionalised is basically determined by the function and construction of the article. It is however preferred to use as large a specific surface as possible. Therefore, for example, particles are desirably as small as possible and fibres have a small diameter, say of the order of 200 microns.

As mentioned above, the time for the functionalisation method of the present invention can be relatively short, for example ten minutes. It is however dependent on the nature (chemical and physical) of the polymer employed. For example, with microporous polypropylene fibres, the preferred conditions are 10 min. at 100° C. (reflux) using 10% w/v aqueous potassium peroxysulphate. Polypropylene and Ecdel films may be functionalised with this reagent; in these cases longer periods of treatment (e.g., up to five hours) are without deleterious effect.

According to the present invention there is also provided a process for the production of a polymer product which comprises reacting a functionalised polymer, formed by the method of the present invention, with another material which could be used for further functionalisation or for coupling to a biomolecular species.

Such other materials may be, for example, (a) vinyl monomers, particularly water-soluble vinyl monomers or mixtures of such monomers, which can be grafted on to the functionalised polymers, and (b) Materials containing other functional groups e.g. those derived from isocyanates, acyl chlorides or acyl anhydrides.

Such reactions include grafting of vinyl monomers by free-radical reactions and/or non-radical introduction of species with various types of functional groups.

Applications include, for example, the treatment of catheters to modify their surface characteristics, notably to reduce friction (Example 10), treatment of hollow-fibre oxygenators and blood filters to improve haemocompatibility (Example 2) and the coupling of a wide range of biomolecules (including antibodies) to polymer supports. Thus molecules to be grafted may include, for example, heparin (Examples 5 and 9), hirudin (Example 8), oligonucleotides and DNA (Example 11), antibacterial agents, the coupling of Cibacron Blue to polymer supports for protein separation and species with groups which promote cell-adhesion.

Grafting of vinyl monomers to non-aromatic hydroxylated polymers is subsequently carried out in aqueous solution by the conventional ceric ion technique. (See G. Mino, S. Kaizerman and S. Rasmussen, *J. Polym. Sci.*, 1958, 31,242). Additionally, grafting of acrylamide by this method may be followed by hydrolysis of the amide groups to carboxyl to provide an increased number of sites for further coupling (see, for example, Example 8). Also grafting of monomers which do not propagate rapidly may be promoted by addition of low concentrations of acrylamide to produce a co-graft (see, for example, Examples 5 and 9).

Alternatively, other functional groups may be introduced by further reactions with the hydroxyls; for example the latter may be reacted with molecules carrying isocyanate groups. Hydroxylated aromatic nuclei in polymers do not normally react with ceric ion in the above way, but the hydroxyls may be reacted with standard reagents, which may, however, require non-aqueous media (see, for example, Examples 6, 7).

The functionalised polymer, as exemplified by the product of reaction step (6) or (7) made with reference to the functionalisation of polypropylene, can thus be subjected to grafting in aqueous solution with, for example, the aid of $Ce^{IV}$. Such a reaction would proceed as follows:

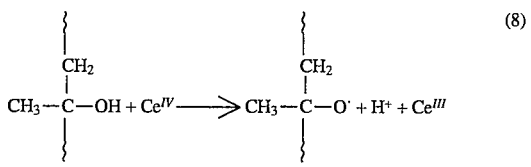

(8)

Thus, for example, water-soluble vinyl monomers ($CH_2=CHR$) e.g., acrylamide or N-vinyl pyrrolidone could be grafted. Such a reaction is considered to be initiated as follows (9):

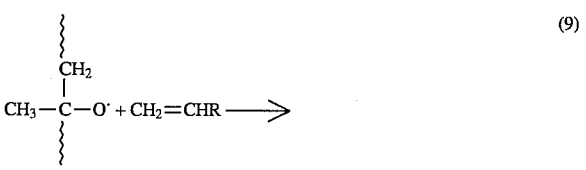

(9)

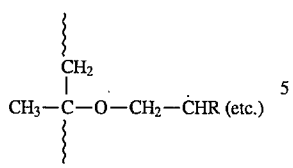

As is apparent from equation (3), oxygen is evolved during thermolysis of peroxysulphate in water and is probably responsible for causing some degradation in certain polymers. With long treatments this may be significant in some forms for example microporous fibres. It is suggested that this degradation arises from the formation of peroxyradicals by addition of oxygen to radical species. Such a reaction scheme might be as follows: (10; 11). This scheme is again exemplified with reference to polypropylene.

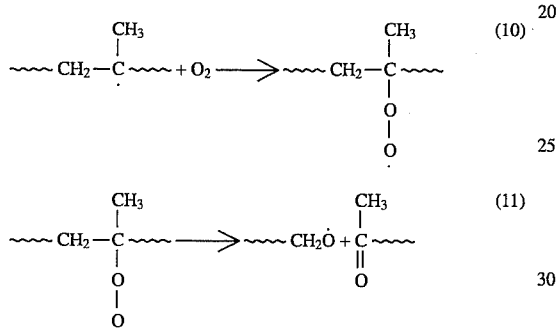

Such radicals could lead to chain scission as in equation (11).

The major process competing with the chain scission in (11) would be hydrogen abstraction forming the hydroxyperoxide, but this is probably less favourable, energetically.

Peroxide has not been detected in the products from polypropylene after hydroxylation. Furthermore, grafting has not been obtained when a film of polypropylene hydroxylated by the method of the present invention is treated with acrylamide in the absence of $Ce^{IV}$.

It has been observed that passing nitrogen through the liquid during hydroxylation to lower the oxygen concentration reduces the chance of degradation, in support of the reaction scheme shown in (10) and (11).

Functionalisation of an aliphatic polyester containing (esterified) 1,4-cyclohexane dimethanol units (sold under the Trade Name "Ecdel"), has been carried out similarly. A typical reaction could be:

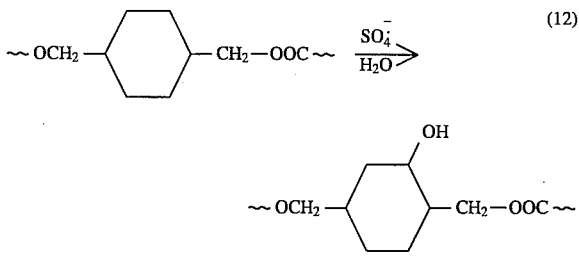

Grafting of a vinyl monomer to the hydroxylated polyester formed in (12) may be carried out in aqueous medium by the ceric ion technique as outlined (cf. equation (8)).

With aromatic polymers hydroxylation may proceed as indicated in (13) for poly(ethylene terephthalate).

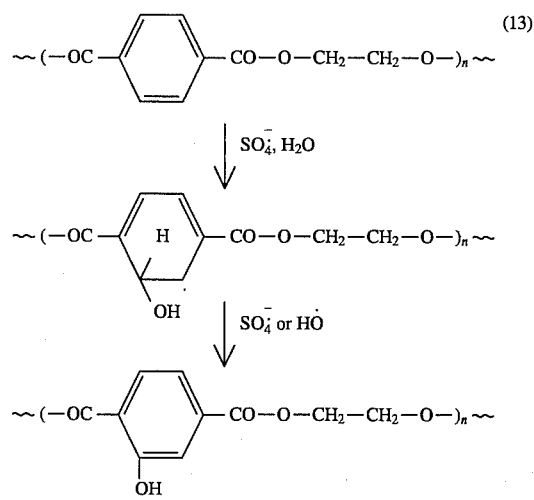

The phenolic OH does not react readily with $Ce^{IV}$ but may be reacted with isocyanates etc., for further functionalisation. Polycarbonates containing aromatic rings behave similarly.

The present invention will now be further described with reference to, but is in no manner limited to, the following Examples.

EXAMPLES

Example 1—Hydroxylation of Polyproylene

Bundles (18 cm×4 cm) of microporous hollow polypropylene fibres, having a diameter of approximately 200 microns, from an oxygenator were heated under reflux with an aqueous solution of potassium peroxydisulphate under the conditions shown in Table 1. In each case a stream of nitrogen was passed through the liquid continuously. Weight and number-average molecular weight after treatment ($M_w$, $M_n$, respectively) are presented in Table 1 and show reductions which are rather small, especially for the shorter reaction time (numbers 2 and 3).

TABLE 1

| Molecular weights of hydroxylated polypropylene fibers. | | | | |
|---|---|---|---|---|
| Sample number | Concentration of $K_2S_2O_8$, % w/v | Reaction time, min. | $\bar{M}_w \times 10^{-3}$ | $\bar{M}_n \times 10^{-3}$ |
| 1 | Control | | 567 | 86 |
|   |         | | 566 | 85 |
| 2 | 5  | 10 | 450 | 80 |
|   |    |    | 447 | 80 |
| 3 | 10 | 10 | 423 | 84 |
|   |    |    | 422 | 77 |
| 4 | 10 | 60 | 361 | 64 |
|   |    |    | 359 | 63 |
| 5 | 5  | 60 | 259 | 58 |
|   |    |    | 258 | 56 |

Some mechanical properties (measured with the aid of a NENE Instron instrument) are shown in Table 2.

These results suggest that concentrations up to 10% w/v with reaction times twenty minutes or less do not produce serious degradation or deterioration in mechanical properties of these specimens.

TABLE 2

Mechanical properties of single hollow fibers of polypropylene after hydroxylation.

| Sample number | Conditions of hydroxylation | | Stress at peak MPa | % Strain at peak |
|---|---|---|---|---|
| | Concentration of $K_2S_2O_8$, % w/v | Reaction time, min. | | |
| 1 | Control | | 36 | 630 |
| | | | 42 | 807 |
| 3 | 10 | 10 | 49 | 746 |
| | | | 42 | 792 |
| 4 | 10 | 60 | 24 | 464 |
| 5 | 5 | 60 | 31 | 545 |
| | | | 29 | 498 |
| 6 | 10 | 20 | 30 | 747 |
| | | | 33 | 686 |

Example 2—Grafting to Hydroxylated Propropylene Fibre

A sample of hydroxylated polypropylene hollow fibres prepared as for Sample number 3, Tables 1 and 2, was submitted to grafting with acrylamide. 0.2 g of the hydroxylated sample was placed in a solution (100 ml) of acrylamide (20% w/v) in 0.04M nitric acid containing ceric ammonium nitrate (0.15 g). The solution was flushed with nitrogen then heated at 50° C. for three hours. The grafted specimen was then washed copiously with water to remove any ungrafted polyacrylamide. The (hydrated) hydrophilic polymer produced in this way had a surface so slippery that handling was difficult. It dyed strongly with Trypan Blue.

A control of non-hydroxylated polypropylene fibres submitted to the same treatment did not show any grafting.

Example 3—Grafting to Hydroxylated Propropylene Films

A polypropylene film (obtained from Goodfellow) (5 cm×5 cm×0.0013 cm) was heated at 80° C. with aqueous potassium peroxydisulphate solution (10% w/v) for two hours. After washing, the film was grafted with acrylamide as in Example 2, then again washed copiously with water. The film so obtained was very hydrophilic and stained strongly with Trypan Blue. The infrared spectra of the film showed strong absorption at 3351 and 3199 cm$^{-1}$ (N-H stretch, Amide A) and 1662 cm$^{-1}$ (C=O stretch) arising from grafted polyacrylamide. No such bands were observed with the control film of polypropylene.

Example 4—Hydroxylation of Ecdel

Hydroxylation of the polyester sold under the Trade Name Ecdel (obtained from Kodak) was carried out on films (3 cm×3 cm×0.014 cm) refluxed in aqueous potassium peroxydisulphate solution (10% w/v) for half an hour. After washing, the films were grafted with acrylamide (20% w/v) in 0.04M $HNO_3$ with $2\times10^{-3}$M ceric ammonium nitrate at 40° C. for times ten minutes, thirty minutes, one hour, two hours and three hours. The grafted films were washed copiously with water and dried in vacuum at 40° C. All the films were found to be stained strongly with Trypan Blue; under comparable conditions the depth of colour appeared proportional to the time of grafting. The ten-minute film showed intense absorption in the infrared, corresponding to the N-H and C=O stretching bands mentioned in Example 3. Percentage weights of polyacrylamide grafted on to hydroxylated Ecdel film are shown in Table 3.

Table 3—Grafting of Polyacrylamide to Hydroxylated Ecdel. Hydroxylation Time ½ h, with 10% w/v Aqueous $K_2S_2O_8$. Film Dimensions 3×3×0.014 cm.

| Sample number | Grafting time, h | % weight increase, w/w |
|---|---|---|
| 1 | 1 | 30.4 |
| 2 | 2 | 49.3 |
| 3 | 3 | 60.0 |
| Control | 3 | 0.33 |

Molecular weights of Ecdel in films before and after hydroxylation are i shown in Table 4. They indicate that negligible change has occurred during the process of hydroxylation.

TABLE 4

Molecular weights of Ecdel in hydroxylated

| Sample number | Concentration of $K_2S_2O_8$, % w/v | Reaction time, min | $\bar{M}_w \times 10^{-3}$ | $\bar{M}_n \times 10^{-3}$ |
|---|---|---|---|---|
| 1 | Control | | 117 | 37 |
| | | | 114 | 38 |
| 2 | 5 | 10 | 117 | 36 |
| | | | 107 | 41 |
| 3 | 5 | 60 | 112 | 37 |
| 4 | 10 | 10 | 113 | 39 |
| | | | 117 | 38 |
| 5 | 10 | 60 | 118 | 37 |
| | | | 118 | 37 |

Some mechanical properties of the hydroxylated Ecdel films are presented in Table 5. The hydroxylation process apparently had little effect on these properties.

TABLE 5

Mechanical properties of hydroxylated Ecdel

| Sample number | Conditions of hydroxylation | | Stress at peak MPa | % Strain at peak |
|---|---|---|---|---|
| | Concentration of $K_2S_2O_8$, % w/v | Reaction time, min. | | |
| Control | | | 31 | 488 |
| | | | 32 | 503 |
| | | | 32 | 533 |
| 1 | 10 | 10 | 26 | 387 |
| | | | 32 | 514 |
| | | | 32 | 506 |
| 2 | 10 | 60 | 30 | 509 |
| | | | 27 | 427 |
| | | | 30 | 530 |

Example 5—Grafting of Heparin Macromer on to Ecdel

Heparin macromer (as described in International Patent Application GB91/00679) and acrylamide were co-grafted at 25° C. to hydroxylated Ecdel film using the ceric ion technique already outlined. Hydroxylation had been performed on a 4 cm×3×0.014 cm Ecdel film, by treatment with 10% aqueous $K_2S_2O_8$ for four hours under reflux. The subsequent co-grafting was carried out with 0.1 g acrylamide, 0.3 g heparin macromer in a total volume of 6 ml for two hours. After very copious and prolonged washing of the film, the bioactivity was assessed by standard measurements of the partial thromboplastin time (PTT). Two controls were used—untreated Ecdel, and Ecdel grafted with acrylamide without heparin.

The following PTTs were recorded for films 1.5×0.5×0.014 cm in 200 µl human plasma plus 200 µl platelet substituent plus 200 µl $CaCl_2$ solution 25 mM.

Ecdel film, untreated: 330 seconds

Ecdel grafted with acrylamide: 460 seconds

Ecdel grafted with herapin and acylamide: 1400 seconds

Clearly the thrombogenicity of the film has been markedly reduced by coupling heparin.

Example 6—Functionalisation of Polycarbonate

Films of polycarbonate (obtained from Goodfellow) (5 cm×5 cm×0.075 cm) were refluxed with 10% w/v aqueous $K_2S_2O_8$ for five hours, then copiously washed in water. The hydroxylated films could not be grafted with the aid of the normal ceric ion technique (equation (8)). However, the hydroxyl groups were found to react readily with tolylene 2,4-diisocyanate (TDI) at 50° C. The product was reacted with Jeffamine (O,O'-bis(2-aminopropyl)ethylene glycol 400) to give a basic polymer:

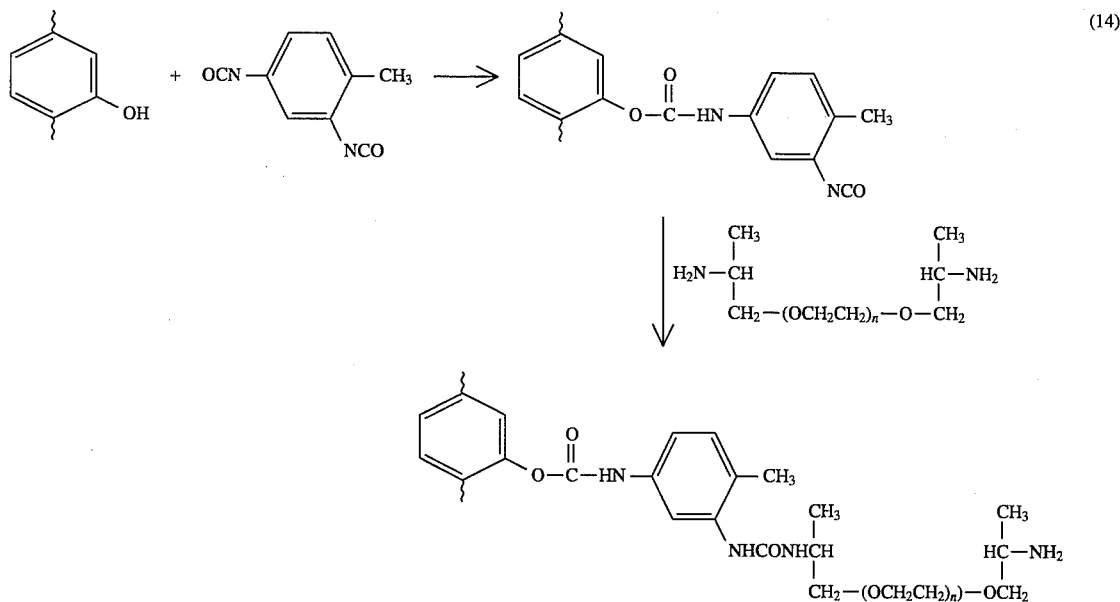

(14)

The final aminated polymer was found to dye very strongly with Eosin-Y. A non-hydroxylated polycarbonate treated with Jeffamine as above failed to give any stain with the dye.

The aminated polymer is clearly suitable for further direct coupling e.g., of biomolecules containing carboxyl.

Example 7—Functionalisation of Poly(Ethylene Terephthalate)

Granules (approximately 1 mm in diameter) of a poly(ethylene terephthalate) sold under the Trade Name Dacron were refluxed in aqueous solution of $K_2S_2O_8$ (10% w/w), washed and dried. The product, like the polycarbonate in Example 6, could not be grafted by the ceric ion technique. It was treated with bulk chlorosulphonyl isocyanate (CSI) (W. A. Szabo, Aldrichimica Acta, 1977, 10, 23) for two hours at 90° C. The product, after washing with petroleum ether was reacted with Jeffamine. After washing it was found to dye strongly with Eosin-Y. The reaction which occurs with CSI is probably that shown in (15).

(15)

Coupling with Jeffamine then proceeds as in equation (12).

Alternatively, the hydroxylated Dacron could be reacted with a diisocyanate as described in Example 6.

Example 8

A polystyrene film was hydroxylated according to the method of the present invention (described for polypropylene in Example 3) then grafted with acrylamide by the ceric ion technique. The polyacrylamide was then hydrolysed by treatment with 1N NaOH at 60° C. for 15 minutes, after which the film was washed extensively with water. The resulting material gave a positive test for COOH with Toluidine Blue. 10 $cm^2$ of the film was activated by reaction with carbonyl diimidazole (2 g in 50 ml acetonitrile, 4 hours at 25° C. then washed, dried in vacuum and coupled with hirudin (10 mg in 1 ml sodium borate buffer, pH, overnight). After prolonged washing with water a portion of the film (1.5×0.5 cm) was submitted to the PTT test (as described in Example 5) with the following result.

After hirudin coupling: 1300 seconds

Control (activated polystyrene): 300 seconds

Example 9

A hydroxylated film:of Ecdel (Example 4) was grafted with a mixture of acrylamide (0.2 g) and 3-aminopropyl methacrylamide hydrochloride (0.8 g) by the ceric ion technique. After washing with 0.5N NaOH the film gave a positive test for amino with Eosin Y. A portion (3×1 cm) was coupled with heparin (0.3 g) in 5 ml water with the aid of 0.3 g EDC (1-ethyl-3-(3-dimethyl aminopropyl carbodimide hydrochloride) (25° C., 17 hours). It was then washed extensively with water and PBS; a piece of the film (2×1 cm) submitted to the PTT test gave the following result.

After heparin coupling: 750 seconds

Control: 230 seconds

Example 10

Catheters were of three types:

(1) composed of nylon-11, (2) having a shaft of Pellethane and a balloon of Tecoflex, and (3) constructed of poly(ether-ester). All were heated at 60° C. in a 10% solution (w/v) of potassium peroxy disulphate for 1 hour then washed extensively. They were then grafted with polyacrylamide by immersion in a solution at 40° C. of acrylamide (10% w/v), ceric ammonium nitrate $5 \times 10^{-3}$M in 0.04M nitric acid. After washing the catheters extensively with hot water, the surface friction was found to be very greatly reduced so that the catheters were very slippery.

Example 11

A disc 2.54 cm in diameter was cut from a membrane of polyacrylonitrile produced by electrostatic spinning or the precipitation technique and hydroxylated by treatment with 10% aqueous potassium peroxydisuplphate at 80° C. for 1 hour. It was then washed copiously with hot water. Oligodeoxythymidine (oligo(dT)) radiolabled with $P^{32}$ was converted to a polymerisable monomer by esterification with 2-hydroxyethyl methacrylate in pyridine solution in the presence of dicyclohexyl carbodiimide. The resulting monomer was grafted to the polyacrylonitrile membrane with acrylamide as comonomer, with the aid of the ceric ion technique described in earlier Examples. The membrane was washed and found to have high radioactivity, indicating that coupling of the oligo(dT) had been achieved.

We claim:

1. A method of producing a functionalized polymer, which method comprises reacting a polymer selected from the group consisting of olefin polymers, aliphatic polyesters, polymers that contain an aromatic ring, carbonate polymers, vinyl polymers, polyurethanes, nylons, polyglycols and polyaldehydes in an aqueous medium with a peroxidant to produce oxygen-centered radicals which are responsible for introducing hydroxyl groups into the polymer, the reaction being carried out in the absence of (a) any additive which is preferentially oxidized or is reactive towards the radicals produced by the peroxidant, (b) added oxygen and (c) a cationic surfactant.

2. A method as claimed in claim 1, in which the peroxidant is a peroxymonosulphate.

3. A method as claimed in claim 2, wherein the peroxidant is a peroxydisulphate.

4. A method as claimed in claim 1, wherein the peroxidant is the salt of an alkalimetal.

5. A method as claimed in claim 1, in which the peroxidant is the potassium or sodium salt of an alkalimetal.

6. A method as claimed in any claim 1 in which the oxidising agent is used in an amount of from 2 to 50% wt/vol.

7. A method as claimed in claim 1 wherein the method is conducted at a temperature of from 40° to 100° C. for a period of from 10 minutes to 5 hours.

8. A method as claimed in claim 1, additionally comprising a step of lowering the oxygen concentration.

9. A method as claimed in claim 8, additionally comprising a step of passing nitrogen into the aqueous medium during the reaction.

10. A method as claimed in claim 1, additionally comprising a step of reacting the functionalized polymer with another material which could be used for further functionalization; or for coupling to a biomolecular species.

11. A method as claimed in claim 10, wherein a biomolecular species is coupled by a free radical reaction or a non radical reaction.

12. A method as claimed in claim 10, wherein the functionalized polymer is reacted with acrylamide or N-vinyl pyrrolidone and the resulting polymer product is formed into a catheter.

13. A method as claimed in claim 10, wherein the functionalized polymer is reacted with acrylamide or N-vinyl pyrrolidone and the resulting polymer product is formed into a hollow fiber oxygenator or a blood filter.

14. A method as claimed in claim 10, wherein the functionalized polymer is reacted with acrylamide or N-vinyl pyrrolidone.

15. A method as claimed in claim 10, additionally comprising a step of coupling the functionalized polymer to a biomolecular species.

16. A method as claimed in claim 1, wherein the functionalized polymer is reacted with a vinyl monomer.

17. A method as claimed in claim 1, wherein the polymer is polypropylene.

18. A method as claimed in claim 1, wherein the polymer is a nylon.

19. A method as claimed in claim 1, wherein the polymer is a polyurethane.

* * * * *